US005747317A

United States Patent [19]
Cao

[11] Patent Number: 5,747,317
[45] Date of Patent: May 5, 1998

[54] HUMAN TELOMERASE RNA INTERACTING PROTEIN GENE

[75] Inventor: Zhaodan Cao, Pacifica, Calif.

[73] Assignee: Tularik Inc., South San Francisco, Calif.

[21] Appl. No.: 676,967

[22] Filed: Jul. 8, 1996

[51] Int. Cl.$^6$ .............................. C12N 9/12; C12N 1/20; C12N 15/00; C07H 21/04

[52] U.S. Cl. .................. 435/194; 435/252.3; 435/320.1; 435/91.31; 536/23.1; 536/23.2; 536/24.31; 530/350

[58] Field of Search .................. 435/194, 7.1, 91.1, 435/240.1, 254.11, 252.3, 320.1, 69.1, 172.3; 530/350; 536/23.1, 23.2

[56] References Cited

U.S. PATENT DOCUMENTS 5,583,016  12/1996  Villeponteau et al. ............... 435/91.3

OTHER PUBLICATIONS

Counter et al. Proc. Natl. Acad. Sci. USA, vol. 91, pp. 2900–2904, Apr. 1, 1994.

*Primary Examiner*—Robert A. Wax
*Assistant Examiner*—Tekchand Saidha
*Attorney, Agent, or Firm*—Richard Aron Osman

[57] ABSTRACT

The invention provides methods and compositions relating to a human telomerase and related nucleic acids, including four distinct human telomerase subunit proteins called p140, p105, p48 and p43 having human telomerae-specific activity. The proteins may be produced recombinantly from transformed host cells from the disclosed telomerase encoding nucleic acids or purified from human cells. Also included are human telomerase RNA components, as well as specific, functional derivative thereof. The invention provides isolated telomerase hybridization probes and primers capable of specifically hybridizing with the disclosed telomerase gene, telomerase-specific binding agents such as specific antibodies, and methods of making and using the subject compositions in diagnosis, therapy and in the biopharmaceutical industry.

10 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 759 amino acids
( B ) TYPE: amino acid
( C ) STRANDEDNESS:
( D ) TOPOLOGY: Not Relevant ( i i ) MOLECULE TYPE: peptide ( x i ) SEQUENCE DESCRIPTION: SEQ ID NO:1:

```
Met Ala Gly Leu Thr Leu Phe Val Gly Arg Leu Pro Pro Ser Ala Arg
 1               5                  10                  15

Ser Glu Gln Leu Glu Glu Leu Phe Ser Gln Val Gly Pro Val Lys Gln
               20                  25                  30

Cys Phe Val Val Thr Glu Lys Gly Ser Lys Ala Cys Arg Gly Phe Gly
           35                  40                  45

Tyr Val Thr Phe Ser Met Leu Glu Asp Val Gln Arg Ala Leu Lys Glu
       50                  55                  60

Ile Thr Thr Phe Glu Gly Cys Lys Ile Asn Val Thr Val Ala Lys Lys
65                  70                  75                  80

Lys Leu Arg Asn Lys Thr Lys Glu Lys Gly Lys Asn Glu Asn Ser Glu
                85                  90                  95

Cys Pro Lys Lys Glu Pro Lys Ala Lys Lys Ala Lys Val Ala Asp Lys
               100                 105                 110

Lys Ala Arg Leu Ile Ile Arg Asn Leu Ser Phe Lys Cys Ser Glu Asp
           115                 120                 125

Asp Leu Lys Thr Val Phe Ala Gln Phe Gly Ala Val Leu Glu Val Asn
       130                 135                 140

Ile Pro Arg Lys Pro Asp Gly Lys Met Arg Gly Phe Gly Phe Val Gln
145                 150                 155                 160

Phe Lys Asn Leu Leu Glu Ala Gly Lys Ala Leu Lys Gly Met Asn Met
                165                 170                 175

Lys Glu Ile Lys Gly Arg Thr Val Ala Val Asp Trp Ala Val Ala Lys
               180                 185                 190

Asp Lys Tyr Lys Asp Thr Gln Ser Val Ser Ala Ile Gly Glu Glu Lys
           195                 200                 205

Ser His Glu Ser Lys His Gln Glu Ser Val Lys Lys Lys Gly Arg Glu
       210                 215                 220

Glu Glu Asp Met Glu Glu Glu Asn Asp Asp Asp Asp Asp Asp Asp Asp
225                 230                 235                 240

Asp Glu Glu Asp Gly Val Phe Asp Asp Glu Asp Glu Glu Glu Glu Asn
                245                 250                 255

Ile Glu Ser Lys Val Thr Lys Pro Val Gln Ile Gln Lys Arg Ala Val
               260                 265                 270

Lys Arg Pro Ala Pro Ala Lys Ser Ser Asp His Ser Glu Glu Asp Ser
           275                 280                 285

Asp Leu Glu Glu Ser Asp Ser Ile Asp Asp Gly Glu Glu Leu Ala Gln
       290                 295                 300

Ser Asp Thr Ser Thr Glu Glu Gln Glu Asp Lys Ala Val Gln Val Ser
305                 310                 315                 320
```

```
Asn Lys Lys Lys Arg Lys Leu Pro Ser Asp Val Asn Glu Gly Lys Thr
                325             330                 335
Val Phe Ile Arg Asn Leu Ser Phe Asp Ser Glu Glu Glu Leu Gly
            340             345             350
Glu Leu Leu Gln Gln Phe Gly Glu Leu Lys Tyr Val Arg Ile Val Leu
            355             360             365
His Pro Asp Thr Glu His Ser Lys Gly Cys Ala Phe Ala Gln Phe Met
370             375             380
Thr Gln Glu Ala Ala Gln Lys Cys Leu Leu Ala Ala Ser Pro Glu Asn
385             390             395                     400
Glu Ala Gly Gly Leu Lys Leu Asp Gly Arg Gln Leu Lys Val Asp Leu
            405             410             415
Ala Val Thr Arg Asp Glu Ala Ala Lys Leu Gln Thr Thr Lys Val Lys
            420             425             430
Lys Pro Thr Gly Thr Arg Asn Leu Tyr Leu Ala Arg Glu Gly Leu Ile
            435             440             445
Arg Ala Gly Thr Lys Ala Ala Glu Gly Val Ser Ala Ala Asp Met Ala
    450             455             460
Lys Arg Glu Arg Phe Glu Leu Leu Lys His Gln Lys Leu Lys Asp Gln
465             470             475             480
Asn Ile Phe Val Ser Arg Thr Arg Leu Cys Leu His Asn Leu Pro Lys
                485             490             495
Ala Val Asp Asp Lys Gln Leu Arg Lys Leu Leu Ser Ala Thr Ser
                500             505             510
Gly Glu Lys Gly Val Arg Ile Lys Glu Cys Arg Val Met Arg Asp Leu
            515             520             525
Lys Gly Val His Gly Asn Met Lys Gly Gln Ser Leu Gly Tyr Ala Phe
    530             535             540
Ala Glu Phe Gln Glu His Glu His Ala Leu Lys Ala Leu Arg Leu Ile
545             550             555             560
Asn Asn Asn Pro Glu Ile Phe Gly Pro Leu Lys Arg Pro Ile Val Glu
                565             570             575
Phe Ser Leu Glu Asp Arg Arg Lys Leu Lys Met Lys Glu Leu Arg Ile
            580             585             590
Gln Arg Ser Leu Gln Lys Met Arg Ser Lys Pro Ala Thr Gly Glu Pro
    595             600             605
Gln Lys Gly Gln Pro Glu Pro Ala Lys Asp Gln Gln Gln Lys Ala Ala
    610             615             620
Gln His His Thr Glu Glu Gln Ser Lys Val Pro Pro Glu Gln Lys Arg
625             630             635             640
Lys Ala Gly Ser Thr Ser Trp Thr Gly Phe Gln Thr Lys Ala Glu Val
            645             650             655
Glu Gln Val Glu Leu Pro Asp Gly Lys Lys Arg Arg Lys Val Leu Ala
            660             665             670
Leu Pro Ser His Arg Gly Pro Lys Ile Arg Leu Arg Asp Lys Gly Lys
        675             680             685
Val Lys Pro Val His Pro Lys Lys Pro Lys Pro Gln Ile Asn Gln Trp
    690             695             700
Lys Gln Glu Lys Gln Gln Leu Ser Ser Glu Gln Val Ser Arg Lys Lys
705             710             715             720
Ala Lys Gly Asn Lys Thr Glu Thr Arg Phe Asn Gln Leu Val Glu Gln
            725             730             735
Tyr Lys Gln Lys Leu Leu Gly Pro Ser Lys Gly Ala Pro Leu Ala Lys
            740             745             750
```

```
Arg  Ser  Lys  Trp  Phe  Asp  Ser
          755
```

( 2 ) INFORMATION FOR SEQ ID NO:2:

( i ) SEQUENCE CHARACTERISTICS:
      ( A ) LENGTH: 2277 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:2:

```
ATGGCNGGNY   TNACNYTNTT   YGTNGGNMGN   YTNCCNCCNW   SNGCNMGNWS   NGARCARYTN     60
GARGARYTNT   TYWSNCARGT   NGGNCCNGTN   AARCARTGYT   TYGTNGTNAC   NGARAARGGN    120
WSNAARGCNT   GYMGNGGNTT   YGGNTAYGTN   ACNTTYWSNA   TGYTNGARGA   YGTNCARMGN    180
GCNYTNAARG   ARATHACNAC   NTTYGARGGN   TGYAARATHA   AYGTNACNGT   NGCNAARAAR    240
AARYTNMGNA   AYAARACNAA   RGARAARGGN   AARAAYGARA   AYWSNGARTG   YCCNAARAAR    300
GARCCNAARG   CNAARAARGC   NAARGTNGCN   GAYAARAARG   CNMGNYTNAT   HATHMGNAAY    360
YTNWSNTTYA   ARTGYWSNGA   RGAYGAYYTN   AARACNGTNT   TYGCNCARTT   YGGNGCNGTN    420
YTNGARGTNA   AYATHCCNMG   NAARCCNGAY   GGNAARATGM   GNGGNTTYGG   NTTYGTNCAR    480
TTYAARAAYY   TNYTNGARGC   NGGNAARGCN   YTNAARGGNA   TGAAYATGAA   RGARATHAAR    540
GGNMGNACNG   TNGCNGTNGA   YTGGGCNGTN   GCNAARGAYA   ARTAYAARGA   YACNCARWSN    600
GTNWSNGCNA   THGGNGARGA   RAARWSNCAY   GARWSNAARC   AYCARGARWS   NGTNAARAAR    660
AARGGNMGNG   ARGARGARGA   YATGGARGAR   GARGARAAYG   AYGAYGAYGA   YGAYGAYGAY    720
GAYGARGARG   AYGGNGTNTT   YGAYGAYGAR   GAYGARGARG   ARGARAAYAT   HGARWSNAAR    780
GTNACNAARC   CNGTNCARAT   HCARAARMGN   GCNGTNAARM   GNCCNGCNCC   NGCNAARWSN    840
WSNGAYCAYW   SNGARGARGA   YWSNGAYYTN   GARGARWSNG   AYWSNATHGA   YGAYGGNGAR    900
GARYTNGCNC   ARWSNGAYAC   NWSNACNGAR   GARCARGARG   AYAARGCNGT   NCARGTNWSN    960
AAYAARAARA   ARMGNAARYT   NCCNWSNGAY   GTNAAYGARG   GNAARACNGT   NTTYATHMGN   1020
AAYYTNWSNT   TYGAYWSNGA   RGARGARGAR   YTNGGNGARY   TNYTNCARCA   RTTYGGNGAR   1080
YTNAARTAYG   TNMGNATHGT   NYTNCAYCCN   GAYACNGARC   AYWSNAARGG   NTGYGCNTTY   1140
GCNCARTTYA   TGACNCARGA   RGCNGCNCAR   AARTGYYTNY   TNGCNGCNWS   NCCNGARAAY   1200
GARGCNGGNG   GNYTNAARYT   NGAYGGNMGN   CARYTNAARG   TNGAYYTNGC   NGTNACNMGN   1260
GAYGARGCNG   CNAARYTNCA   RACNACNAAR   GTNAARAARC   CNACNGGNAC   NMGNAAYYTN   1320
TAYYTNGCNM   GNGARGGNYT   NATHMGNGCN   GGNACNAARG   CNGCNGARGG   NGTNWSNGCN   1380
GCNGAYATGG   CNAARMGNGA   RMGNTTYGAR   YTN YTNAARC   AYCARAARYT   NAARGAYCAR   1440
AAYATHTTYG   TNWSNMGNAC   NMGNYTNTGY   YTNCAYAAYY   TNCCNAARGC   NGTNGAYGAY   1500
AARCARYTNM   GNAARYTNYT   NYTNWSNGCN   ACNWSNGGNG   ARAARGGNGT   NMGNATHAAR   1560
GARTGYMHEREGNG   TNATGMGNGA   YYTNAARGGN   GT-
NCAYGGNA   AYATGAARGG   NCARWSNYTN       1620
GGNTAYGCNT   TYGCNGARTT   YCARGARCAY   GARCAYGCNY   TNAARGCNYT   NMGNYTNATH   1680
AAYAAYAAYC   CNGARATHTT   YGGNCCNYTN   AARMGNCCNA   THGTNGARTT   YWSNYTNGAR   1740
GAYMGNMGNA   ARYTNAARAT   GAARGARYTN   MGNATHCARM   GNWSNYTNCA   RAARATGMGN   1800
WSNAARCCNG   CNACNGGNGA   RCCNCARAAR   GGNCARCCNG   ARCCNGCNAA   RGAYCARCAR   1860
```

| | | | | | |
|---|---|---|---|---|---|
| CARAARGCNG | CNCARCAYCA | YACNGARGAR | CARWSNAARG | TNCCNCCNGA | RCARAARMGN | 1920 |
| AARGCNGGNW | SNACNWSNTG | GACNGGNTTY | CARACNAARG | CNGARGTNGA | RCARGTNGAR | 1980 |
| YTNCCNGAYG | GNAARAARMG | NMGNAARGTN | YTNGCNYTNC | CNWSNCAYMG | NGGNCCNAAR | 2040 |
| ATHMGNYTNM | GNGAYAARGG | NAARGTNAAR | CCNGTNCAYC | CNAARAARCC | NAARCCNCAR | 2100 |
| ATHAAYCART | GGAARCARGA | RAARCARCAR | YTNWSNWSNG | ARCARGTNWS | NMGNAARAAR | 2160 |
| GCNAARGGNA | AYAARACNGA | RACNMGNTTY | AAYCARYTNG | TNGARCARTA | YAARCARAAR | 2220 |
| YTNYTNGGNC | CNWSNAARGG | NGCNCCNYTN | GCNAARMGNW | SNAARTGGTT | YGAYWSN | 2277 |

(2) INFORMATION FOR SEQ ID NO:3:

(i) SEQUENCE CHARACTERISTICS:
        (A) LENGTH: 2733 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| TGAGCTTGGT | TGTCCTACCA | AAGCCAGCGT | TTCGGCTCGC | GTGCGCCGGC | CTAGTTTGCT | 60 |
| CGCGTCCTCA | CGCGCTTTGG | GTTTCCGGT | CTCATGGCCG | GCCTGACCTT | ATTTGTGGGC | 120 |
| CGCCTCCCGC | CCTCGGCCCG | CAGTGAGCAG | CTGGAGGAAC | TGTTCAGTCA | GGTGGGGCCG | 180 |
| GTGAAGCAGT | GCTTCGTGGT | GACTGAAAAA | GGGAGTAAGG | CATGTCGAGG | CTTTGGCTAT | 240 |
| GTCACTTTTT | CAATGCTGGA | AGATGTTCAG | AGGGCCCTCA | AGGAGATTAC | CACCTTTGAA | 300 |
| GGTTGCAAGA | TCAACGTGAC | TGTTGCCAAG | AAAAAACTGA | GGAACAAGAC | AAAGGAAAAG | 360 |
| GGGAAAAATG | AAAACTCAGA | GTGCCCAAAG | AAGGAGCCGA | AGGCTAAAAA | AGCCAAAGTG | 420 |
| GCAGATAAGA | AAGCCAGATT | AATTATTCGG | AACCTGAGCT | TTAAGTGTTC | AGAAGATGAC | 480 |
| TTGAAGACAG | TATTTGCTCA | ATTTGGAGCT | GTCCTGGAAG | TAAATATCCC | TAGGAAACCA | 540 |
| GATGGGAAGA | TGCGCGGTTT | TGGTTTTGTT | CAGTTCAAAA | ACCTCCTAGA | AGCAGGTAAA | 600 |
| GCTCTCAAAG | GCATGAACAT | GAAAGAGATA | AAAGGCCGGA | CAGTGGCTGT | GGATTGGGCC | 660 |
| GTGGCAAAGG | ATAAATATAA | AGATACACAG | TCTGTTTCTG | CTATAGGTGA | GGAAAAGAGC | 720 |
| CATGAATCTA | AACATCAGGA | ATCAGTTAAA | AAGAAGGGCA | GAGAGGAAGA | GGATATGGAA | 780 |
| GAGGAAGAAA | ACGATGATGA | TGACGATGAT | GATGATGAAG | AAGATGGGGT | TTTTGATGAT | 840 |
| GAAGATGAAG | AGGAAGAGAA | TATAGAATCA | AAGGTGACCA | AGCCTGTGCA | AATTCAGAAG | 900 |
| AGAGCAGTCA | AGAGACCAGC | CCCTGCAAAA | AGCAGTGATC | ATTCTGAGGA | GGACAGTGAC | 960 |
| CTAGAGGAAA | GCGATAGTAT | TGATGATGGA | GAGGAACTGG | CTCAGAGTGA | TACCAGCACT | 1020 |
| GAGGAGCAAG | AGGATAAAGC | TGTGCAAGTC | TCAAACAAAA | AGAAGAGGAA | ATTACCCTCT | 1080 |
| GATGTGAATG | AAGGGAAAAC | TGTTTTTATC | AGAAATCTGT | CCTTTGACTC | AGAAGAAGAA | 1140 |
| GAACTTGGGG | AGCTTCTCCA | ACAGTTTGGA | GAACTCAAAT | ATGTCCGCAT | TGTCTTGCAT | 1200 |
| CCAGACACAG | AGCATTCTAA | AGGTTGTGCA | TTTGCCCAGT | TCATGACTCA | AGAAGCAGCT | 1260 |
| CAGAAATGCC | TTCTAGCTGC | TTCTCCAGAG | AATGAGGCTG | GTGGGCTTAA | ACTGGATGGC | 1320 |
| CGGCAGCTCA | AGGTTGACTT | GGCGGTGACC | CGTGATGAGG | CTGCAAAGCT | TCAGACGACG | 1380 |
| AAGGTGAAGA | AGCCGACTGG | CACCCGGAAT | CTCTATCTGG | CCCGAGAAGG | CTTGATTCGT | 1440 |
| GCTGGGACGA | AGGCTGCAGA | GGGTGTGAGT | GCTGCTGATA | TGGCCAAAAG | AGAACGGTTT | 1500 |
| GAGCTGCTGA | AGCATCAGAA | ACTCAAGGAC | CAGAATATCT | TTGTCTCCCG | AACCAGGCTC | 1560 |
| TGCCTGCACA | ATCTCCCAAA | GGCTGTAGAT | GACAAACAGC | TCAGAAAGCT | GCTGCTGAGT | 1620 |

```
GCTACTAGTG  GAGAGAAAGG  GGTGCGCATC  AAGGAGTGTA  GAGTGATGCG  AGACCTCAAA   1680

GGAGTTCATG  GGAACATGAA  GGGTCAGTCC  CTGGGCTACG  CCTTTGCGGA  GTTCCAAGAG   1740

CACGAGCATG  CCCTGAAAGC  CCTCCGCCTC  ATCAACAACA  ATCCAGAAAT  CTTTGGGCCT   1800

CTGAAGAGAC  CAATAGTGGA  GTTCTCTTTA  GAAGATCGAA  GAAAACTTAA  AATGAAGGAA   1860

TTAAGGATCC  AGCGCAGCTT  GCAAAAAATG  AGATCCAAGC  CTGCAACTGG  TGAGCCTCAG   1920

AAGGGGCAAC  CAGAGCCTGC  AAAAGACCAG  CAACAGAAGG  CAGCTCAACA  CCACACAGAG   1980

GAACAAAGCA  AGGTGCCCCC  AGAGCAGAAG  AGAAGGCGG   GCTCTACCTC  ATGGACCGGG   2040

TTCCAGACCA  AGGCTGAAGT  GGAGCAGGTG  GAGCTGCCTG  ATGGAAAGAA  GAGAAGAAAG   2100

GTCCTGGCGC  TCCCCTCACA  CCGAGGCCCC  AAAATCAGGT  TGCGGGACAA  AGGCAAAGTG   2160

AAGCCCGTCC  ATCCCAAAAA  GCCAAAGCCA  CAGATAAACC  AGTGGAAGCA  GGAGAAGCAG   2220

CAATTATCGT  CCGAGCAGGT  ATCTAGGAAA  AAAGCTAAGG  GAAATAAGAC  GGAAACCCGC   2280

TTCAACCAGC  TGGTCGAACA  ATATAAGCAG  AAATTATTGG  GACCTTCTAA  AGGAGCACCT   2340

CTTGCAAAGA  GGAGCAAATG  GTTGATAGT   TGATGATGGC  AGCAGGCTGG  GTAAGAAGCT   2400

GGGTTGTATA  CTTTCTGGTG  ACACTCCTGG  GCTCCTCCCC  ATCCCCGTG   TCTCTCACTG   2460

AGGGAAAGAA  AATCCCCAAG  GGCACTGCCA  CTGTGCTCGG  AGGTGCCCTG  GACTGTGTAC   2520

ATCTGAACTT  TGGTCCATCC  TTTGATGTGT  GGTTCGTTAG  CCACAAAGAG  AAATATCTGA   2580

AAGTCAACAT  GATGCTTCTT  GCATATTATC  CAGATTATTG  TATGAAGTTG  TGTCTATAAT   2640

TATTACCAAT  TTTTATTCTT  TATTTCTCAA  ATGGAAACAC  CTGAAAAAGC  AAAAAAAAAA   2700

AAAAAAAAAA  CTCGAGGGGG  GCCCGTACCC  AAT                                  2733
```

( 2 ) INFORMATION FOR SEQ ID NO:4:

( i ) SEQUENCE CHARACTERISTICS:
        ( A ) LENGTH: 2277 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
AUGGCUGGUC  UGACCCUGUU  CGUUGGUCGU  CUGCCGCCGU  CCGCUCGUUC  CGAACAGCUG    60

GAAGAACUGU  UCUCCCAGGU  UGGUCCGGUU  AAACAGUGCU  UCGUUGUUAC  CGAAAAGGU    120

UCCAAAGCUU  GCCGUGGUUU  CGGUUACGUU  ACCUUCUCCA  UGCUGGAAGA  CGUUCAGCGU   180

GCUCUGAAAG  AAAUCACCAC  CUUCGAAGGU  UGCAAAAUCA  CGUUACCGU   UGCUAAAAAA   240

AAACUGCGUA  ACAAAACCAA  AGAAAAAGGU  AAAAACGAAA  ACUCCGAAUG  CCCGAAAAAA   300

GAACCGAAAG  CUAAAAAAGC  UAAAGUUGCU  GACAAAAAAG  CUCGUCUGAU  CAUCCGUAAC   360

CUGUCCUUCA  AAUGCUCCGA  AGACGACCUG  AAAACCGUUU  UCGCUCAGUU  CGGUGCUGUU   420

CUGGAAGUUA  ACAUCCCGCG  UAAACCGGAC  GGUAAAUGC   GUGGUUUCGG  UUUCGUUCAG   480

UUCAAAAACC  UGCUGGAAGC  UGGUAAAGCU  CUGAAAGGUA  UGAACAUGAA  AGAAAUCAAA   540

GGUCGUACCG  UUGCUGUUGA  CUGGGCUGUU  GCUAAAGACA  AAUACAAAGA  CACCCAGUCC   600

GUUUCCGCUA  UCGGUGAAGA  AAAAUCCCAC  GAAUCCAAAC  ACCAGGAAUC  CGUUAAAAAA   660

AAAGGUCGUG  AAGAAGAAGA  CAUGGAAGAA  GAAGAAAACG  ACGACGACGA  CGACGACGAC   720

GACGAAGAAG  ACGGUGUUUU  CGACGACGAA  GACGAAGAAG  AAGAAAACAU  CGAAUCCAAA   780

GUUACCAAAC  CGGUUCAGAU  CCAGAAACGU  GCUGUUAAAC  GUCCGGCUCC  GGCUAAAUCC   840
```

| | | | | | |
|---|---|---|---|---|---|
| UCCGACCACU | CCGAAGAAGA | CUCCGACCUG | GAAGAAUCCG | ACUCCAUCGA | CGACGGUGAA 900 |
| GAACUGGCUC | AGUCCGACAC | CUCCACCGAA | GAACAGGAAG | ACAAAGCUGU | UCAGGUUUCC 960 |
| AACAAAAAAA | AACGUAAACU | GCCGUCCGAC | GUUAACGAAG | GUAAACCGU | UUUCAUCCGU 1020 |
| AACCUGUCCU | UCGACUCCGA | AGAAGAAGAA | CUGGGUGAAC | UGCUGCAGCA | GUUCGGUGAA 1080 |
| CUGAAAUACG | UUCGUAUCGU | UCUGCACCCG | GACACCGAAC | ACUCCAAAGG | UUGCGCUUUC 1140 |
| GCUCAGUUCA | UGACCCAGGA | AGCUGCUCAG | AAAUGCCUGC | UGGCUGCUUC | CCCGGAAAAC 1200 |
| GAAGCUGGUG | GUCUGAAACU | GGACGGUCGU | CAGCUGAAAG | UUGACCUGGC | UGUUACCCGU 1260 |
| GACGAAGCUG | CUAAACUGCA | GACCACCAAA | GUUAAAAAAC | CGACCGGUAC | CCGUAACCUG 1320 |
| UACCUGGCUC | GUGAAGGUCU | GAUCCGUGCU | GGUACCAAAG | CUGCUGAAGG | UGUUUCCGCU 1380 |
| GCUGACAUGG | CUAAACGUGA | ACGUUUCGAA | CUGCUGAAAC | ACCAGAAACU | GAAAGACCAG 1440 |
| AACAUCUUCG | UUUCCCGUAC | CCGUCUGUGC | CUGCACAACC | UGCCGAAAGC | UGUUGACGAC 1500 |
| AAACAGCUGC | GUAAACUGCU | GCUGUCCGCU | ACCUCCGGUG | AAAAGGUGU | UCGUAUCAAA 1560 |
| GAAUGCCGUG | UUAUGCGUGA | CCUGAAAGGU | GUUCACGGUA | ACAUGAAAGG | UCAGUCCCUG 1620 |
| GGUUACGCUU | UCGCUGAAUU | CCAGGAACAC | GAACACGCUC | UGAAAGCUCU | GCGUCUGAUC 1680 |
| AACAACAACC | CGGAAAUCUU | CGGUCCGCUG | AAACGUCCGA | UCGUUGAAUU | CUCCCUGGAA 1740 |
| GACCGUCGUA | AACUGAAAAU | GAAAGAACUG | CGUAUCCAGC | GUUCCCUGCA | GAAAAUGCGU 1800 |
| UCCAAACCGG | CUACCGGUGA | ACCGCAGAAA | GGUCAGCCGG | AACCGGCUAA | AGACCAGCAG 1860 |
| CAGAAAGCUG | CUCAGCACCA | CACCGAAGAA | CAGUCCAAAG | UUCCGCCGGA | ACAGAAACGU 1920 |
| AAAGCUGGUU | CCACCUCCUG | GACCGGUUUC | CAGACCAAAG | CUGAAGUUGA | ACAGGUUGAA 1980 |
| CUGCCGGACG | GUAAAAAACG | UCGUAAAGUU | CUGGCUCUGC | CGUCCCACCG | UGGUCCGAAA 2040 |
| AUCCGUCUGC | GUGACAAAGG | UAAAGUUAAA | CCGGUUCACC | CGAAAAAACC | GAAACCGCAG 2100 |
| AUCAACCAGU | GGAAACAGGA | AAAACAGCAG | CUGUCCUCCG | AACAGGUUUC | CCGUAAAAAA 2160 |
| GCUAAAGGUA | ACAAAACCGA | AACCCGUUUC | AACCAGCUGG | UUAACAGUA | CAAACAGAAA 2220 |
| CUGCUGGGUC | CGUCCAAAGG | UGCUCCGCUG | GCUAAACGUU | CCAAAUGGUU | CGACUCC 2277 |

(2) INFORMATION FOR SEQ ID NO:5:

(i) SEQUENCE CHARACTERISTICS:
    (A) LENGTH: 2277 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:5:

| | | | | | |
|---|---|---|---|---|---|
| ATGGCCGGCC | TGACCCTGTT | CGTGGGCCGC | CTGCCCCCCA | GCGCCCGCAG | CGAGCAGCTG 60 |
| GAGGAGCTGT | TCAGCCAGGT | GGGCCCCGTG | AAGCAGTGCT | TCGTGGTGAC | CGAGAAGGGC 120 |
| AGCAAGGCCT | GCCGCGGCTT | CGGCTACGTG | ACCTTCAGCA | TGCTGGAGGA | CGTGCAGCGC 180 |
| GCCCTGAAGG | AGATCACCAC | CTTCGAGGGC | TGCAAGATCA | ACGTGACCGT | GGCCAAGAAG 240 |
| AAGCTGCGCA | ACAAGACCAA | GGAGAAGGGC | AAGAACGAGA | CAGCGAGTG | CCCCAAGAAG 300 |
| GAGCCCAAGG | CCAAGAAGGC | CAAGGTGGCC | GACAAGAAGG | CCCGCCTGAT | CATCCGCAAC 360 |
| CTGAGCTTCA | AGTGCAGCGA | GGACGACCTG | AAGACCGTGT | CGCCCAGTT | CGGCGCCGTG 420 |
| CTGGAGGTGA | ACATCCCCCG | CAAGCCCGAC | GGCAAGATGC | GCGGCTTCGG | CTTCGTGCAG 480 |
| TTCAAGAACC | TGCTGGAGGC | CGGCAAGGCC | CTGAAGGGCA | TGAACATGAA | GGAGATCAAG 540 |
| GGCCGCACCG | TGGCCGTGGA | CTGGGCCGTG | GCCAAGGACA | AGTACAAGGA | CACCCAGAGC 600 |

| | | | | | |
|---|---|---|---|---|---|
| GTGAGCGCCA | TCGGCGAGGA | GAAGAGCCAC | GAGAGCAAGC | ACCAGGAGAG | CGTGAAGAAG | 660 |
| AAGGGCCGCG | AGGAGGAGGA | CATGGAGGAG | GAGGAGAACG | ACGACGACGA | CGACGACGAC | 720 |
| GACGAGGAGG | ACGGCGTGTT | CGACGACGAG | GACGAGGAGG | AGGAGAACAT | CGAGAGCAAG | 780 |
| GTGACCAAGC | CCGTGCAGAT | CCAGAAGCGC | GCCGTGAAGC | GCCCCGCCCC | CGCCAAGAGC | 840 |
| AGCGACCACA | GCGAGGAGGA | CAGCGACCTG | GAGGAGAGCG | ACAGCATCGA | CGACGGCGAG | 900 |
| GAGCTGGCCC | AGAGCGACAC | CAGCACCGAG | GAGCAGGAGG | ACAAGGCCGT | GCAGGTGAGC | 960 |
| AACAAGAAGA | AGCGCAAGCT | GCCCAGCGAC | GTGAACGAGG | GCAAGACCGT | GTTCATCCGC | 1020 |
| AACCTGAGCT | TCGACAGCGA | GGAGGAGGAG | CTGGGCGAGC | TGCTGCAGCA | GTTCGGCGAG | 1080 |
| CTGAAGTACG | TGCGCATCGT | GCTGCACCCC | GACACCGAGC | ACAGCAAGGG | CTGCGCCTTC | 1140 |
| GCCCAGTTCA | TGACCCAGGA | GGCCGCCCAG | AAGTGCCTGC | TGGCCGCCAG | CCCCGAGAAC | 1200 |
| GAGGCCGGCG | GCCTGAAGCT | GGACGGCCGC | CAGCTGAAGG | TGGACCTGGC | CGTGACCCGC | 1260 |
| GACGAGGCCG | CCAAGCTGCA | GACCACCAAG | GTGAAGAAGC | CCACCGGCAC | CCGCAACCTG | 1320 |
| TACCTGGCCC | GCGAGGGCCT | GATCCGCGCC | GGCACCAAGG | CCGCCGAGGG | CGTGAGCGCC | 1380 |
| GCCGACATGG | CCAAGCGCGA | GCGCTTCGAG | CTGCTGAAGC | ACCAGAAGCT | GAAGGACCAG | 1440 |
| AACATCTTCG | TGAGCCGCAC | CCGCCTGTGC | CTGCACAACC | TGCCCAAGGC | CGTGGACGAC | 1500 |
| AAGCAGCTGC | GCAAGCTGCT | GCTGAGCGCC | ACCAGCGGCG | AGAAGGGCGT | GCGCATCAAG | 1560 |
| GAGTGCCGCG | TGATGCGCGA | CCTGAAGGGC | GTGCACGGCA | ACATGAAGGG | CCAGAGCCTG | 1620 |
| GGCTACGCCT | TCGCCGAGTT | CCAGGAGCAC | GAGCACGCCC | TGAAGGCCCT | GCGCCTGATC | 1680 |
| AACAACAACC | CCGAGATCTT | CGGCCCCCTG | AAGCGCCCCA | TCGTGGAGTT | CAGCCTGGAG | 1740 |
| GACCGCCGCA | AGCTGAAGAT | GAAGGAGCTG | CGCATCCAGC | GCAGCCTGCA | GAAGATGCGC | 1800 |
| AGCAAGCCCG | CCACCGGCGA | GCCCCAGAAG | GGCCAGCCCG | AGCCGCCAA | GGACCAGCAG | 1860 |
| CAGAAGGCCG | CCCAGCACCA | CACCGAGGAG | CAGAGCAAGG | TGCCCCCGA | GCAGAAGCGC | 1920 |
| AAGGCCGGCA | GCACCAGCTG | GACCGGCTTC | CAGACCAAGG | CCGAGGTGGA | GCAGGTGGAG | 1980 |
| CTGCCCGACG | GCAAGAAGCG | CCGCAAGGTG | CTGGCCCTGC | CCAGCCACCG | CGGCCCCAAG | 2040 |
| ATCCGCCTGC | GCGACAAGGG | CAAGGTGAAG | CCCGTGCACC | CCAAGAAGCC | CAAGCCCCAG | 2100 |
| ATCAACCAGT | GGAAGCAGGA | GAAGCAGCAG | CTGAGCAGCG | AGCAGGTGAG | CCGCAAGAAG | 2160 |
| GCCAAGGGCA | ACAAGACCGA | GACCCGCTTC | AACCAGCTGG | TGGAGCAGTA | CAAGCAGAAG | 2220 |
| CTGCTGGGCC | CCAGCAAGGG | CGCCCCCCTG | GCCAAGCGCA | GCAAGTGGTT | CGACAGC | 2277 |

( 2 ) INFORMATION FOR SEQ ID NO:6:

( i ) SEQUENCE CHARACTERISTICS:
  ( A ) LENGTH: 540 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| GGGTTGCGGA | GGGTGGGCCT | GGGAGGGGTG | GTGGCCATTT | TTTGTCTAAC | CCTAACTGAG | 60 |
| AAGGGCGTAG | GCGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACCGCG | 300 |

| AAGAGTTGGG | CTCTGTCAGC | CGCGGGTCTC | TCGGGGGCGA | GGGCGAGGTT | CAGGCCTTTC | 360 |
| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:7:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| GGGTTGCGGA | GGGTGGGCCT | GGGAGGGGTG | GTGGCCATTT | TTTGTCCAAC | CCCAACTGAG | 60 |
| AAGGGCGTAG | GCGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACCGCG | 300 |
| AAGAGTTGGG | CTCTGTCAGC | CGCGGGTCTC | TCGGGGGCGA | GGGCGAGGTT | CAGGCCTTTC | 360 |
| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:8:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

| GGGTTGCGGA | GGGTGGGCCT | GGGAGGGGTG | GTGGCCATTT | TTTGTCTAAG | CCTAAGTGAG | 60 |
| AAGGGCGTAG | GCGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACCGCG | 300 |
| AAGAGTTGGG | CTCTGTCAGC | CGCGGGTCTC | TCGGGGGCGA | GGGCGAGGTT | CAGGCCTTTC | 360 |
| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:9:

( i ) SEQUENCE CHARACTERISTICS:
        ( A ) LENGTH: 538 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GGGTTGCGGA  GGGTGGGCCT  GGGAGGGGTG  GTGGCCATTT  TTTGTCTACC  CTACTGAGAA    60
GGGCGTAGGC  GCCGTGCTTT  TGCTCCCCGC  GCGCTGTTTT  TCTCGCTGAC  TTTCAGCGGG   120
CGGAAAAGCC  TCGGCCTGCC  GCCTTCCACC  GTTCATTCTA  GAGCAAACAA  AAAATGTCAG   180
CTGCTGGCCC  GTTCGCCCCT  CCCGGGGACC  TGCGGCGGGT  CGCCTGCCCA  GCCCCCGAAC   240
CCCGCCTGGA  GGCCGCGGTC  GGCCCGGGGC  TTCTCCGGAG  GCACCCACTG  CCACCGCGAA   300
GAGTTGGGCT  CTGTCAGCCG  CGGGTCTCTC  GGGGGCGAGG  GCGAGGTTCA  GGCCTTTCAG   360
GCCGCAGGAA  GAGGAACGGA  GCGAGTCCCC  GCGCGCGGCG  CGATTCCCTG  AGCTGTGGGA   420
CGTGCACCCA  GGACTCGGCT  CACACATGCA  GTTCGCTTTC  CTGTTGGTGG  GGGGAACGCC   480
GATCGTGCGC  ATCCGTCACC  CCTCGCCGGC  AGTGGGGGCT  TGTGAACCCC  CAAACCTG    538
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Peptide
        ( B ) LOCATION: 5..13
        ( D ) OTHER INFORMATION: /note="Xaa represents isoleucine or leucine"

( x i ) SEQUENCE DESCRIPTION: SEQ ID NO:10:

```
Glu  Ala  Ala  Thr  Xaa  Asp  Xaa  Pro  Gln  Gln  Gly  Ala  Asn  Lys
 1             5                        10
```

HUMAN TELOMERASE RNA INTERACTING PROTEIN GENE

FIELD OF THE INVENTION

The field of this invention is a human gene encoding an enzyme involved in cell replication.

BACKGROUND

DNA at chromosome ends is maintained in a dynamic balance of loss and addition of telomeric simple sequence repeats. Sequence loss occurs during cell replication, in part from incomplete replication of chromosome termini by DNA-dependent DNA polymerase. Telomeric repeat addition is catalyzed by the enzyme telomerase: a ribonucleoprotein enzyme which uses a short region within the RNA as a template for the polymerase reaction. Although cells can maintain a constant number of telomeric repeats by balancing repeat loss and addition, not all cells do so. Human germline and cancer cells maintain a constant number of telomeric repeats, while normal human somatic cells lose telomeric repeats with each cycle of cell division. Cells which do not maintain stable telomere length demonstrate a limited proliferative capacity: these cells senesce after a number of population doublings correlated with the erosion of telomeres to a critical minimum length.

Because normal somatic cells do not appear to express or require telomerase and do not maintain chromosome ends, and because all or almost all cancer cells express high levels of telomerase activity and maintain chromosome ends, molecules that inhibit or alter telomerase activity could provide effective and non-toxic anti-cancer agents. Similarly, inhibition of telomerase in parasitic or infectious agents (e.g. trypanosomes, fungi, etc.) could provide a specific approach for reducing the viability or proliferation of these agents. Conversely, activation of telomerase in proliferation-restricted cells (such as normal somatic cells of the blood, vasculature, liver, skin, etc.) could provide a mechanism for promoting additional proliferative lifespan.

Relevant Literature

Purification of telomerase from the ciliate Tetrahymena and cloning of genes encoding two protein components of the enzyme is reported in Collins et al. (1995) Cell 81, 677–686 and copending U.S. patent application Ser. No. 08/359,125, filed 19 Dec., 1994. Literature relating to human telomerase include Kim et al. (1994) Science 266, 2011–2014; and Feng et al. (1995) Science 269, 1236–1241. Literature relating to telomerase template modifications include Autexier et al. (1994) Genes and Devel 8, 563–575; Yu et al. (1991) Cell 67, 823–832; and Yu et al. (1990) Nature 344, 126–132. The Washington University-Merck EST Project contains an EST, reportedly deposited by Hillier et al. on Nov. 1, 1995, which has sequence similarity with the 3' end of SEQ ID NO:3, disclosed herein. For a general review, see Blackburn et al., Eds. (1995) Telomeres, Cold Spring Harbor Laboratory Press.

SUMMARY OF THE INVENTION

The invention provides methods and compositions relating to a human telomerase and related nucleic acids. Included are four distinct human telomerase subunit proteins, called p140, p105, p48 and p43 telomerase protein domains thereof having telomerase-specific activity. The proteins may be produced recombinantly from transformed host cells from the subject telomerase encoding nucleic acids or purified from human cells. Also included are human telomerase RNA components, as well as specific, functional derivatives thereof.

The invention provides isolated telomerase hybridization probes and primers capable of specifically hybridizing with the disclosed telomerase gene, telomerase-specific binding agents such as specific antibodies, and methods of making and using the subject compositions in diagnosis (e.g. genetic hybridization screens for telomerase transcripts), therapy (e.g. gene therapy to modulate telomerase gene expression) and in the biopharmaceutical industry (e.g. reagents for screening chemical libraries for lead pharmacological agents and nucleic acid polymerase reagents).

SEQ ID LISTING

SEQ ID NO:1: p105 protein (amino acid sequence)
SEQ ID NO:2: p105 ambiguity maximized synthetic DNA
SEQ ID NO:3: p105 natural cDNA (the coding region is bp 97-2370)
SEQ ID NO:4: p105 E. coli optimized synthetic DNA
SEQ ID NO:5: p105 mammalian optimized synthetic DNA
SEQ ID NO:6: telomerase RNA
SEQ ID NO:7: telomerase RNA template region modification 1
SEQ ID NO:8: telomerase RNA template region modification 2
SEQ ID NO:9: telomerase RNA template region modification 3
SEQ ID NO:10 p43 peptide (XXXEAAT[I/L]D[I/L]PQQGANK, where the three X's are indeterminant residues)

DETAILED DESCRIPTION OF THE INVENTION

The invention provides isolated human telomerase proteins including human telomerase proteins p140, p105, p48 and p43, having molecular weights of about 140kD, about 105kD, about 48kD and about 43kD, respectively, as determined by polyacrylamide gel electrophoresis under denaturing conditions (Matsudaira and Burgess (1978) Anal Biochem 87, 386–396), and telomerase protein domains thereof. The telomerase proteins comprise assay-discernable functional domains including RNA recognition motifs and subunit binding domains and may be provided as fusion products, e.g. with non-telomerase polypeptides. The human telomerase proteins of the invention, including the subject protein domains, all have telomerase-specific activity or function.

Telomerase-specific activity or function may be determined by convenient in vitro, cell-based or in vivo assays: e.g. in vitro binding assays, cell culture assays, in animals (e.g. immune response, gene therapy, transgenics, etc.), etc. Binding assays encompass any assay where the molecular interaction of a telomerase protein with a binding target is evaluated. The binding target may be a natural intracellular binding target such as a telomerase subunit (e.g. another protein subunit or RNA subunit), a substrate, agonist, antagonist, chaperone, or other regulator that directly modulates telomerase activity or its localization; or non-natural binding target such a specific immune protein such as an antibody, or a telomerase specific agent such as those identified in assays described below. Generally, telomerase-binding specificity is assayed by telomere polymerase activity (see, e.g. Collins et al. 1995, Cell 81, 677–686), by binding equilibrium constants (usually at least about $10^7 M^{-1}$, preferably at least about $10^8 M^{-1}$, more preferably at least about $10^9 M^{-1}$), by the ability of the subject protein to function as negative mutants in telomerase-expressing cells, to elicit telomerase specific antibody in a heterologous host (e.g. a rodent or rabbit), etc. In any event, the telomerase binding specificity of the subject telomerase proteins necessarily distinguishes ciliate telomerase, preferably distinguishes non-mammalian telomerases and more preferably distinguishes non-human telomerases. Exemplary telomerase proteins which are shown to have telomerase binding specificity include the telomerase RNA (e.g. SEQ ID NO:6) binding domains (e.g. RRM 1–4: SEQ ID NO:1, about residues 5–81, residues 115–192, residues 336–420, and residues 487–578, respectively), telomerase primer binding domains, nucleotide triphosphate binding domains and binding domains of regulators of telomerase such as nuclear localization proteins, etc. As used herein, a protein domain comprises at least 12, preferably at least about 20, more preferably at least about 40, most preferably at least about 80 residues of the disclosed respective SEQ ID NO.

The claimed human telomerase proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The telomerase proteins and protein domains may be synthesized, produced by recombinant technology, or purified from human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York) or that are otherwise known in the art. An exemplary method for isolating each of human telomerase protein p140, p105, p48 and p43 from human cells is as follows:

Several thousand (two to twelve thousand) liters of HeLa cells are grown in spinner culture. The cells are lysed by dounce homogenization in low-salt buffer to produce crude cell lysates. The lysates are supplemented with 15% glycerol and centrifuged at 125,000×g for 50 minutes to obtain a first soluble fraction enriched for telomerase activity (S-100 fraction). The S-100 fraction is adjusted to 0.2M ammonium sulfate, bound to SP Sepharose (Pharmacia), and developed with a gradient in sodium chloride, to obtain a second soluble fraction enriched for telomerase (SP fraction). The SP fraction is adjusted to about 0.3–0.4M ionic strength and bound to Q Sepharose (Pharmacia), and developed with a gradient in sodium chloride, to obtain a third soluble fraction enriched for telomerase (Q fraction). The Q fraction is adjusted to about 0.3–0.4M ionic strength, bound to phosphocellulose (Whatman), and developed with sodium chloride, to obtain a fourth soluble fraction enriched for telomerase (PC fraction). The PC fraction is adjusted to about 0.3–0.4M ionic strength, bound to 2'Omethyl RNA oligonucleotide immobilized on streptavidin agarose (Sigma), and eluted with a electrophoresis sample medium comprising 5% β-mercaptoethanol and 2% Sodium Dodecyl Sulfate to obtain a fifth soluble fraction (2'Omethyl fraction). The 2'Omethyl fraction is separated by polyacrylamide gel electrophoresis under denaturing conditions (Matsudaira and Burgess (1978) Anal Biochem 87, 386–396) to obtain gel protein bands at a molecular weight of about 140kD, 105kD, 48kD or 43kD having telomerase activity. The gel bands are excised or blotted to obtain purified human telomerase proteins p140, p105, p48 and p43.

The subject telomerase proteins find a wide variety of uses including use in isolating, enriching for and concentrating telomerase RNA and telomerase proteins, as immunogens, in the methods and applications described below, as reagents in the biotechnology industries, and in therapy. Recombinant telomerase are used in many applications where nascent oligonucleotides of predetermined sequence are desired. For example, native nucleic acid molecules are labeled or extended at their 3' ends by addition of a predetermined repeat sequence (for double-stranded oligonucleotides, both ends of the molecule may be tagged). Oligonucleotides complementary to the repeat are then used to amplify, sequence, affinity purify, etc. the nucleic acid molecules. The use of a repeat sequence for 3' end tagging improves specificity and provides sequence alternatives compared with non-templated enzymes presently available for this purpose, e.g. terminal transferase. Repeats encoding restriction enzyme sites provide repeat tagging to facilitate cloning and the use of telomerase alleviates the restrictive conditions required for optimal ligation with available ligase enzymes. Telomerase also finds use in regulating cell growth or increasing cell density tolerance; for example, cells contacted with an effective amount of exogenous telomerase to overcome the growth control limitation otherwise imposed by short telomere length. Telomerase may be introduced, expressed, or repressed in specific populations of cells by any convenient way such as microinjection, promoter-specific expression of recombinant enzyme, targeted delivery of lipid vesicles, etc. Advantageously, only a brief period of telomerase activity is required to allow many generations of continued proliferation of the contacted cell, due to the ability of telomerase to extend telomeres in one cell cycle by more sequence than is lost with each cell division.

The invention provides natural and non-natural human telomerase-specific binding agents including substrates, agonist, antagonist, etc., methods of identifying and making such agents, and their use in diagnosis, therapy and pharmaceutical development. For example, human telomerase-specific agents are useful in a variety of diagnostic and therapeutic applications. Novel human telomerase-specific binding agents include human telomerase-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate human telomerase function, e.g. human telomerase antagonists and find use methods for modulating the binding of a human telomerase or telomerase protein to a human telomerase binding target.

For diagostic uses, the binding agents are frequently labeled, such as with fluorescent, radioactive, chemilumninescent, or other easily detectable molecules, either conjugated directly to the binding agent or conjugated to a probe specific for the binding agent. Binding agents also find use in modulating the telomerase activity present in a cell. For example, isolated cells, whole tissues, or individuals may be treated with a telomerase binding agent to activate, inhibit, or alter the specificity of telomerase assembly, localization, substrate interaction, or synthesis activity. Effectively treated cells have increased or decreased replication potential, or suffer from loss of proper telomere structure (resulting in lethality). These binding agents also find therapeutic use to control cell proliferation; for example, the uncontrolled growth of transformed cells (e.g. cancer cells) is managed by administration to the cells or patient comprising such cells of a telomerase binding agent which reduces telomerase activity. In contrast to many current chemotherapies, the present invention provides enhanced specificity of lethality, with minimum toxicity to dividing yet normal somatic cells.

The amino acid sequences of the disclosed telomerase proteins are used to back-translate telomerase protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural telomerase encoding nucleic acid sequences ("GCG" software, Genetics Computer Group, Inc, Madison Wis). As examples, SEQ ID NO:2 discloses an ambiguity-maximized p105 coding sequence encompassing all possible nucleic acids encoding the full-length p105 protein. SEQ ID NO:3 discloses a natural human cDNA sequence encoding p105, SEQ ID NO:4 is a p105 coding sequence codon-optimized for *E. coli*, SEQ ID NO:5 is a p105 coding sequence codon optimized for mammalian cell expression. Telomerase encoding nucleic acids may be part of human telomerase-expression vectors and may be incorporated into recombinant host cells, e.g. for expression and screening, transgenic animals, e.g. for functional studies such as the efficacy of candidate drugs for disease associated with human telomerase-mediated signal transduction, etc. Expression systems are selected and/or tailored to effect human telomerase protein structural and functional variants through alternative post-translational processing.

The invention also provides nucleic acid hybridization probes and replication/amplification primers having a human telomerase cDNA specific sequence contained in SEQ ID NO:3, bases 1–2345, and sufficient to effect specific hybridization thereto (i.e. specifically hybridize with SEQ ID NO:3, bases 1–2345 in the presence of natural ciliate telomerase cDNA, preferably in the presence of non-mammalian telomerase cDNA and more preferably, in the presence of murine telomerase cDNA). Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Human telomerase cDNA homologs can also be distinguished from other protein using alignment algorithms, such as BLASTX (Altschul et al. (1990) Basic Local Alignment Search Tool, J Mol Biol 215, 403–410).

The invention also provides non-natural sequence, recombinant and isolated natural sequence human telomerase RNA. Natural human telomerase RNA sequences include the nucleic acid disclosed as SEQ ID NO:6, or a fragment thereof sufficient to specifically hybridize with a nucleic acid having the sequence defined by SEQ ID NO:6 in the presence of a nucleic acid having the sequence disclosed in Feng et al. 1995, Science 269, 1236–1241. Such fragments necessarily distinguish the previously described (Feng et al. 1995, Science 269, 1236–1241) human RNA species. Preferred such fragments comprise SEQ ID NO:6, bases 191–210, bases 245–259, bases 341–369 or bases 381–399. Non-natural sequences include derivatives and/or mutations of SEQ ID NO:6, where such derivatives/mutations provide alteration in template, protein binding, or other regions to effect altered telomerase substrate specificity or altered reaction product (e.g. any predetermined sequence), etc.; see, e.g. Autexier et al., 1994, Genes & Develop 8, 563–575; Collins et al. (1995) EMBO J. 14, 5422–5432; Greider et al. (1995) Structure and Biochemistry of Ciliate and Mammalian Telomerases, in DNA Replication, DePamphlis, Ed., Cold Spring Harbor Laboratory Press. Additional derivatives function as dominant negative fragments which effectively compete for telomerase assembly. For examples, SEQ ID NO:7, 8 and 9 are derivatives which provide for modified substrate specificity and polymerase reaction product to interfere with cellular function (see, e.g. Hanish et al. (1994) Proc Natl Acad Sci 91, 8861–8865).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:3 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is immediately flanked by a sequence other than that which it is joined to on a natural chromosome. While the nucleic acids are usually RNA or DNA, it is often advantageous to use nucleic acids comprising other bases or nucleotide analogs to provide modified stability, etc. The subject nucleic acids find a wide variety of applications including use as translatable transcripts, hybridization probes, PCR primers, diagnostic nucleic acids, etc.; use in detecting the presence of human telomerase genes and gene transcripts and in detecting or amplifying nucleic acids encoding additional human telomerase homologs and structural analogs.

In diagnosis, human telomerase hybridization probes find use in identifying wild-type and mutant human telomerase alleles in clinical and laboratory samples. Mutant alleles are used to generate allele-specific oligonucleotide (ASO) probes for high-throughput clinical diagnoses. In therapy, therapeutic human telomerase nucleic acids are used to modulate cellular expression or intracellular concentration or availability of active telomerase. A wide variety of indications may be treated, either prophylactically or therapeutically with the subject compositions. For example, where limitation of cell growth is desired, e.g. neoproliferative disease, a reduction in telomerase expression is effected by introducing into the targeted cell type human telomerase nucleic acids which reduce the functional expression of human telomerase gene products (e.g. nucleic acids capable of inhibiting translation of a functional telomerase transcript). Conditions for treatment include various cancers, where any of a wide variety of cell types may be involved, restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

Telomerase inhibitory nucleic acids are typically antisense: single-stranded sequences comprising complements of the disclosed natural telomerase coding sequences. Antisense modulation of the expression of a given telomerase protein may employ telomerase antisense nucleic acids operably linked to gene regulatory sequences. Cell are transfected with a vector comprising a human telomerase sequence with a promoter sequence oriented such that transcription of the gene yields an antisense transcript capable of binding to endogenous human telomerase protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given human telomerase protein may be administered to the target cell, in or temporarily isolated from a host, at a concentration that results in a substantial reduction in expression of the targeted protein.

In other indications, e.g. certain hypersensitivities, atrophic diseases, etc., an increase in cell growth or proliferation is desired. In these applications, an enhancement in human telomerase expression is effected by introducing into the targeted cell type human telomerase nucleic acids which increase the functional expression of human telomerase gene products. Conditions for treatment include multiple sclerosis, where certain neuronal cells are involved, inflammatory disease states such as rheumatoid arthritis, where bystander cells are involved, transplant rejection where graft cells are involved, infectious diseases such as HIV infection where certain uninfected host cells are involved, or the like. Such nucleic acids may be human telomerase expression vectors, vectors which upregulate the functional expression of an endogenous human telomerase allele, or replacement vectors for targeted correction of human telomerase mutant alleles.

Various techniques may be employed for introducing of the nucleic acids into viable cells, e.g. transfection with a retrovirus, viral coat protein-liposome mediated transfection. The techniques vary depending upon whether one is using the subject compositions in culture or in vivo in a host. In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The invention provides methods and compositions for enhancing the yield of many recombinantly produced proteins by increasing maximum cell densities and survival time of host production cells in culture. Specifically, cultured cells are transfected with nucleic acids which effect the up-regulation of endogenous telomerase or the expression of an exogenous telomerase. For example, nucleic acids encoding functional human telomerase operably linked to a transcriptional promoter are used to over-express the exogenous telomerase in the host cell. Telomerase-expressing cells demonstrate enhanced survival ability at elevated cell densities and over extended culture periods.

The invention provides efficient methods of identifying agents, compounds or lead compounds for agents active at the level of a human telomerase modulatable cellular function. Generally, these screening methods involve assaying for compounds which modulate human telomerase interaction with a natural human telomerase binding target. A wide variety of assays for binding agents are provided including labeled in vitro telomere polymerase assays, protein—protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc. Target cells also include progenitor cells for repopulating blood or bone marrow, tissue grafts, and tissue subject to degredation/high turnover such as digestive and vascular endothelia and pulmunary and dermal epithelia.

In vitro binding assays employ a mixture of components including a human telomerase protein, which may be part of multi-subunit telomerase, a fusion product with another peptide or polypeptide, e.g. a tag for detection or anchoring, etc. The assay mixtures comprise a natural intracellular human telomerase binding target, e.g. a substrate. While native binding targets may be used, it is frequently preferred to use portions (e.g. peptides, nucleic acid fragments) thereof so long as the portion provides binding affinity and avidity to the subject human telomerase conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the human telomerase specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the human telomerase and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For telomere polymerase assays, binding is detected by a change in the polymerization by the telomerase of a nucleic acid or nucleic acid analog on the substrate.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the human telomerase protein to the target in the absence of the agent as compared with the binding affinity in the presence of the agent indicates that the agent modulates the binding of the human telomerase protein to the human telomerase binding target. Analogously, in the cell-based transcription assay also described below, a difference in the human telomerase transcriptional induction in the presence and absence of an agent indicates the agent modulates human telomerase-induced transcription. A difference, as used herein, is statistically significant and preferably represents at least a 50%, more preferably at least a 90% difference.

The following examples are offered by way of illustration and not by way of limitation.

EXAMPLES

1. Protocol for high-throughput human telomere polymerization assay.

A. Reagents:

Neutralite Avidin:20 μg/ml in PBS.

human telomerase:$10^{-8}$–$10^{-5}$M human telomerase in PBS.

Blocking buffer:5% BSA, 0.5% Tween 20 in PBS; 1 hour at room temperature.

Assay Buffer:100 mM KCl, 20 mM HEPES pH 7.6, 1 mM $MgCl_2$, 1 mM dATP, 1 mM dTTP, 1% glycerol, 0.5% NP-40, 50 mM BME, 1 mg/ml BSA, cocktail of protease inhibitors.

[$^{32}$P]α-dGTP 10×stock:2×$10^5$M "cold" dGTP with 100 μCi [$^{32}$P]α-dGTP. Place in the 4° C. microfridge during screening.

telomerase substrate:$10^{-7}$–$10^{-4}$M biotinylated telomerase substrate (5'-biotin-d (TTAGGG)$_3$-3'] in PBS.

Protease inhibitor cocktail (1000X):10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVo$_3$(Sigma # S-6508) in 10 ml of PBS.

B. Preparation of assay plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl human telomerase (1–1000 fmoles/40 ul in assay buffer)

Add 10 μl compound or extract.

Add 10 μl [$^{32}$P]α-dGTP 10×stock.

Add 40 μl biotinylated telomerase substrate (0.1–10 pmoles/40 μl in assay buffer)

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):
 a. Non-specific binding
 b. cold dGTP at 80% inhibition.

2. Protocol for high throughput human telomerase subunit-RNA complex formation assay.

A. Reagents:

Neutralite Avidin:20 μl/ml in PBS.

Blocking buffer:5% BSA, 0.5% Tween 20 in PBS; 1 hour at room temperature.

Assay Buffer:100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P human telomerase protein 10×stock:$10^{-8}$–$10^{-6}$M "cold" human telomerase subunit (p105) supplemented with 200,000–250,000 cpm of labeled human telomerase (Beckman counter). Place in the 4° C. microfridge during screening.

Protease inhibitor cocktail (1000X):10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM NaVo$_3$ (Sigma # S-6508) in 10 ml of PBS.

telomerase RNA:$10^{-7}$–$10^{-4}$M biotinylated RNA (SEQ ID NO:6) in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-human telomerase protein (20,000–25,000 cpm/0.1–10 pmoles/well=$10^{-9}$–$10^{-7}$M final concentration).

Shake at 25° C. for 15 minutes.

Incubate additional 45 minutes at 25° C.

Add 40 μl biotinylated RNA (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):
 a. Non-specific binding
 b. Soluble (non-biotinylated telomerase) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising SEQ ID NO:3, or a portion thereof at least 36 bases in length and immediately flanked by a native flanking region fewer than 10 kb and encoding a telomerase protein p105 (SEQ ID NO:1) domain having human telomerase-specific activity.

2. An isolated nucleic acid according to claim 1, wherein said domain specifically binds at least one of the telomerase RNA of SEQ ID NO:6, a telomerase subunit, substrate, agonist, antagonist, chaperone, regulatory protein or cytoskeletal protein.

3. An isolated nucleic acid according to claim 1, wherein the portion encodes at least one of SEQ ID NO:1, residues 5–81, 115–192, 336–420 and 487–578.

4. An isolated nucleic acid comprising a portion of SEQ ID NO:3, bases 1–2345, at least 36 bases in length and immediately flanked by a native flanking region fewer than 10 kb and which specifically hybridizes with a nucleic acid having the sequence defined by SEQ ID NO:3 under low stringent conditions.

5. An isolated nucleic acid according to claim 4, wherein the portion is at least 60 bases in length.

6. A method of modulating the expression of a telomerase transcript, said method comprising steps: contacting inside a cell an endogenous transcript encoding a telomerase protein with a nucleic acid according to claim 4 under conditions whereby said nucleic acid hybridizes with said transcript, whereby the expression of said transcript is modulated.

7. A recombinant nucleic acid consisting of an open reading frame comprising SEQ ID NO:3, or a portion thereof at least 60 bases in length sufficient to encode a telomerase protein p105 (SEQ ID NO:1) domain at least 20 residues in length and having human telomerase-specific activity.

8. A recombinant nucleic acid according to claim 7, wherein said open reading frame comprises SEQ ID NO:3, bases 97–2370.

9. A cell comprising a nucleic acid according to claim 7.

10. A method of making an isolated telomerase protein, comprising steps: introducing a nucleic acid according to claim 7 into a host cell or cellular extract, incubating said host cell or extract under conditions whereby said nucleic acid is expressed as a transcript and said transcript is expressed as a translation product comprising said protein, and isolating said translation product.

* * * * *